United States Patent
Ou et al.

(10) Patent No.: US 11,826,796 B2
(45) Date of Patent: Nov. 28, 2023

(54) NON-HAZARDOUS CLEANING SOLUTION AND PROCESS FOR CLEANING BLACKENED NEEDLES

(71) Applicant: Ethicon, Inc., Somerville, NJ (US)

(72) Inventors: Duan Li Ou, Warren, NJ (US); Christophe Vailhe, Hillsborough, NJ (US)

(73) Assignee: Ethicon, Inc., Raritan, NJ (US)

( * ) Notice: Subject to any disclaimer, the term of this patent is extended or adjusted under 35 U.S.C. 154(b) by 0 days.

(21) Appl. No.: 17/545,225

(22) Filed: Dec. 8, 2021

(65) Prior Publication Data

US 2022/0097106 A1 Mar. 31, 2022

Related U.S. Application Data

(62) Division of application No. 16/438,851, filed on Jun. 12, 2019, now Pat. No. 11,213,866.

(51) Int. Cl.
| | | |
|---|---|---|
| *A61B 17/00* | (2006.01) | |
| *B08B 3/12* | (2006.01) | |
| *B08B 3/08* | (2006.01) | |
| *C11D 7/26* | (2006.01) | |

(52) U.S. Cl.
CPC ............... *B08B 3/12* (2013.01); *B08B 3/08* (2013.01); *C11D 7/265* (2013.01)

(58) Field of Classification Search
None
See application file for complete search history.

(56) References Cited

U.S. PATENT DOCUMENTS

| | | |
|---|---|---|
| 865,700 A | 9/1907 | Hernsheim et al. |
| 1,334,092 A | 3/1920 | Harmeling |
| 2,981,633 A | 4/1961 | Davis et al. |
| 4,432,808 A | 2/1984 | Heubusch |
| 4,686,067 A | 8/1987 | Veysset et al. |
| 5,000,912 A | 3/1991 | Bendel et al. |
| 5,181,416 A | 1/1993 | Evans |
| 5,464,477 A | 11/1995 | Awad |
| 5,932,019 A | 8/1999 | Espinoza |
| 6,018,860 A | 2/2000 | Smith et al. |
| 6,635,118 B2 | 10/2003 | Sachdev et al. |
| 7,611,588 B2 | 11/2009 | Peitersen et al. |
| 2003/0114883 A1 | 6/2003 | Roby |
| 2006/0112972 A1 | 6/2006 | Peitersen et al. |
| 2011/0036372 A1 | 2/2011 | Stirling |
| 2013/0186429 A1 | 7/2013 | Morita |
| 2017/0370004 A1 | 12/2017 | Ou et al. |

FOREIGN PATENT DOCUMENTS

| | | |
|---|---|---|
| CN | 103079490 A | 5/2013 |
| CN | 104294292 A | 1/2015 |
| CN | 105970234 A | 9/2016 |
| CN | 109312470 A | 2/2019 |
| DE | 102015222350 A1 | 5/2017 |
| EP | 0168833 A1 | 1/1986 |
| EP | 0908144 A1 | 4/1999 |
| EP | 2617866 A1 | 7/2013 |

OTHER PUBLICATIONS

Espacenet translation of CN 104294292 retrieved from https://worldwide.espacenet.com/patent/search/family/052314235/publication/CN104294292A?q=cn%20104294292 on Jan. 13, 2021 (Year: 2021).*
Chinese Office Action in connection with patent application 202080042920.3, dated Dec. 15, 2022, 10 pages.
Sheffield Metals International, SMI 1" FF Snaplock Plywood Installation Details, Cleaning and Maintenance Guide For Metal Building Components Coated with Sheffield Kynar 500 or Hylar 500 Resin Pain, pp. 1-31, (2012).
Valspar Corporation, Cleaning and Maintenance Guide for Fluoropolymer Coatings, pp. 1-2, received Jul. 27, 2023.

* cited by examiner

*Primary Examiner* — Eric W Golightly
(74) *Attorney, Agent, or Firm* — Amir Bishara

(57) ABSTRACT

A blackened surgical needle made by the method of treating blackened surgical needles, comprising the steps of: a. determining that a blackening process may have produced loose black oxide particles on the blackened surgical needle; b. placing at least one blackened surgical needle having loose black oxide particles on its surface into a bath, wherein the bath comprises: i. an effective amount of citric acid to remove loose black oxide particles from the at least one blackened surgical needle; and ii. a source of ultrasound; and c. applying the ultrasound in the bath for a time sufficient to remove loose black oxide particles from the surface of the at least one needle and wherein the contents of the bath are maintained at a pH below 3.25.

11 Claims, No Drawings

NON-HAZARDOUS CLEANING SOLUTION AND PROCESS FOR CLEANING BLACKENED NEEDLES

CROSS-REFERENCE TO RELATED APPLICATION

This application is a divisional application of co-pending U.S. application Ser. No. 16/438,851 filed on Jun. 12, 2019, and issued as U.S. Pat. No. 11,213,866 on Jan. 4, 2022, the complete disclosure of which is hereby incorporated herein by reference for all purposes.

FIELD OF THE INVENTION

The field of art to which this invention pertains is manufacturing processes for surgical needles, more particularly, processes for removal of metal oxide residues from surgical needles.

BACKGROUND OF THE INVENTION

Surgical needles are typically made from conventional metals such as surgical stainless steels and other biocompatible metal alloys. The needles desirably have smooth outer surfaces to facilitate the passage through tissue and minimize the adherence of contaminants or foreign substances. The needle surfaces are typically polished to provide smooth surfaces that are bright, shiny and reflective. Surgical needles are typically coated with silicone coatings to improve the penetration of the needles through multiple passes in tissue.

In certain types of surgical procedures such as endoscopic and laparoscopic surgical procedures, the surgeon views the site of the procedure remotely via a camera and a screen display of the surgical field. It is known that in such procedures the surgical team may have difficulty in seeing a conventional surgical needle because of the shiny reflective surfaces. This is particularly true of the distal end of the needle having the tissue piercing point. The inability to quickly and efficiently locate the needle and needle tip when conducting a laparoscopic suturing procedure has led to the development of surgical needles having blackened surfaces. The blackened needles have proven to have better visibility in the surgical field and are often preferred in minimally invasive surgical procedures utilizing indirect visualization.

Blackening processes for blackening the bright, shiny surfaces of surgical needles are known in this art. The processes may include chemical baths, exposure to plasmas, laser energy, oxidizing fumes, etc. The objective of the blackening processes is to form an iron oxide ($Fe_3O_4$)-based layer on the surfaces of the stainless steel needles which provides the blackened appearance.

An issue with some of the blackening processes is that loose black oxide residues or particles may remain on the needles after the blackening process. Removal of the loose particles is important as interference of the particles with further coatings on the needles is not desirable as adhesion integrity of the needle coatings themselves may be compromised.

Accordingly, there is a need in this art for novel methods and processes for removing metal oxide residuals from blackened surgical needles that are environmentally friendly, safe, and are cost effective.

SUMMARY OF THE INVENTION

A non-hazardous cleaning solution/process has been developed to remove oxide residues from the surfaces of blackened needles. Low concentrations of citric acid solutions are mixed with blackened needles and treated in an ultrasonic tank for short period of time (<5 minutes). The oxide residue is substantially removed. Quite surprisingly and unexpectedly, the penetration performance of the cleaned needles are greatly improved by up to 50%.

One embodiment of this invention relates to a method of treating blackened surgical needles, comprising the steps of:
 a. placing at least one blackened surgical needle having loose black oxide particles on its surface into a bath, wherein the bath comprises:
  i. an effective amount of citric acid; and
  ii. a source of ultrasound; and
 b. applying the ultrasound in the bath for a time sufficient to remove loose black oxide particles from the surface of the needle.

Another embodiment of this invention relates to a system for treating blackened surgical needles having loose black oxide particles comprising an ultrasonic bath and citric acid.

These and other aspects and advantages of the present invention will become more apparent from the following description.

DETAILED DESCRIPTION OF THE INVENTION

Blackened Needles

The surgical needles that can be blackened and treated by the present invention include conventional surgical needles having conventional shapes made from conventional surgical grade stainless steel alloys. The stainless steel alloys will include but not be limited to Type 455, Type 316, Type 4310, Type 420, and the like. Another type of stainless steel alloy that can be blackened using the processes of the present invention is the proprietary alloy "ETHALLOY" available from Ethicon, Inc., Somerville, N.J. 08876 USA. The composition of ETHALLOY alloy is described in U.S. Pat. No. 5,000,912, which is incorporated by reference. The processes, baths and systems of the present invention can also be used to blacken the surfaces of other types of medical devices, in addition to needles, made from such alloys.

The processing equipment useful for blackening needles include conventional processing equipment such open vats, tanks, mixing apparatus, and baskets. The equipment may include specially designed and adapted tanks for receiving needles on strips when using high speed needle manufacturing processes. The equipment will be made of conventional corrosion resistant materials such as Nylon, glass, PEEK, Teflon, PVDF, and the like. The equipment may be made of conventional metals such as aluminum, and stainless steel that have had their contact surfaces coated with conventional corrosion resistant coatings such as ceramic, PTFE, FEP, and the like.

The needles may be pretreated in baths containing aqueous-based compositions. These pretreatment baths will have sufficient quantities of the bath ingredients to provide for effective pretreatment. The pretreatment baths will typically contain about 8 wt. % to about 20 wt. % of a water soluble chloride salt, more typically about 10 wt. % to about 18 wt. %, and preferably about 15 wt. % to about 17 wt. %. The pretreatment baths will also contain about 5 wt. % to about 15 wt. % of an inorganic acid, more typically about 6 wt. % to about 10 wt. %, and preferably about 7 wt. % to about 8 wt. %. And, the pretreatment baths will typically contain about 60 wt. % to about 90 wt. % of water, more typically about 70 wt. % to about 80 wt. %, and preferably about 75 wt. % to about 78 wt. %. The water soluble chloride salts useful in the pretreatment baths include but are not limited to sodium chloride, potassium chloride, lithium chloride and the like. The inorganic acids useful in the pretreatment baths include but are not limited to phosphoric acid, sulfuric acid, hydrochloric acid, nitric acid, and the like. The pH of the pretreatment baths will typically range from about 0.1 to about 1.2, more typically about 0.3 to about 1, and preferably about 0.5 to about 0.8.

The blackening bath compositions desirably are aqueous-based compositions. The blackening baths will have sufficient quantities of the bath ingredients to provide for effective blackening of the surfaces of needles. The blackening baths will typically contain about 18 wt. % to about 38 wt. % of a strong base, more typically about 20 wt. % to about 35 wt. %, and preferably about 26 wt. % to about 30 wt. %. The blackening baths of the present invention will typically contain about 3 wt. % to about 20 wt. % of a highly soluble nitric acid salt, more typically about 5 wt. % to about 15 wt. %, and preferably about 11 wt. % to about 13 wt. %. And the blackening baths will typically contain about 50 wt. % to about 75 wt. % of water, more typically about 55 wt. % to about 70 wt. %, and preferably about 58 wt. % to about 65 wt. %. The nitric acid salts useful in the blackening baths of the present invention include but are not limited to sodium nitrate, potassium nitrate, lithium nitrate, and the like. The strong bases useful in the blackening baths of the present invention include but are not limited to sodium hydroxide, potassium hydroxide, lithium hydroxide, and the like.

The blackening baths may contain components containing two different precursors to form transition metal sulfides. The first precursor is a transition metal salt of a strong acid. Such precursors include but are not limited to nickel nitrate, cobalt nitrate, nickel sulphate, cobalt sulphate, iron nitrate, copper perchlorate, nickel perchlorate, ion perchlorate, and cobalt perchlorate and the like. The second precursor is a sulfur-containing reducer. Such second precursors include but are not limited to N,N'-diethylthiourea, sodium thiocyanate, sodium sulfide, and sodium dimethyldithiocarbamate and the like. The transition metal sulfide compounds that are formed may include, but are not limited to, NiS, CoS, $Ag_2S$, etc. The amount of the transition metal salt of a strong acid included in this embodiment of the blackening baths of the present invention is typically about 0.1 wt. % to about 3 wt. %, more typically about 0.2 wt. % to about 2 wt. %, and preferably about 0.3 wt. % to about 1 wt. %. The amount of the sulfur-containing reducer included in this embodiment of the blackening baths of the present invention is typically about 0.1 wt. % to about 3 wt. %, more typically about 0.2 wt. % to about 2 wt. %, and preferably about 0.3 wt. % to about 1 wt. %.

In an alternate embodiment, the blackening baths may also contain manganese-containing oxidizers, also referred to as highly soluble permanganate salts, including but not limited to potassium permanganate, sodium permanganate, and lithium permanganate, and the like. The baths in the second embodiment will also contain a thiocyanate salt. The thiocyanate salts useful in this embodiment of the blackening baths include but are not limited to as sodium thiocyanate, potassium thiocyanate, lithium thiocyanate, and the like. The amount of the manganese-containing oxidizer (highly soluble permanganate salt) in this second embodiment of the blackening baths of the present invention is typically about 0.1 wt. % to about 5 wt. %, more typically about 0.2 wt. % to about 3 wt. %, and preferably about 0.3 wt. % to about 1 wt. %. The amount of the thiocyanate salt included in this embodiment of the blackening baths of the present invention is typically about 0.1 wt. % to about 5 wt. %, more typically about 0.2 wt. % to about 3 wt. %, and preferably about 0.3 wt. % to about 1 wt. %.

The alternate embodiment of the blackening baths may optionally include several additives to enhance the color of the black oxide layer, and enable the repeat usage of the blackening bath. The additives include and are not limited to 1. molybdate salts including ammonium molybdate, sodium molybdate and potassium molybdate; and, 2. sodium chloride. The amount of molybdate salts optionally present in this embodiment will be sufficient to provide effective blackening enhancement and would typically range from 0.1 wt. % to about 3 wt. %. The amount of sodium chloride optionally present in this embodiment will be sufficient to provide effective blackening enhancement and would typically range from 0.3 wt. % to about 1 wt. %.

The pretreatment bath compositions and the blackening bath compositions may be made in a conventional manner using conventional process and mixing equipment. For example, the blackening and pretreatment bath compositions may be made in the following manner: mixing all of the components using a mechanical mixer for a sufficiently effective time up to about one hour until all of the solid components are fully dissolved in the aqueous solution.

Desirable methods for blackening surgical needles consist of two primary steps. The initial step is a pretreatment step that is performed prior to the needle blackening step. In the pretreatment step surface oxides are removed from the surfaces of the needles. The second step is the needle blackening step. In the blackening step, a black oxide coating is formed on the surfaces of the needles.

The pretreatment step is directed toward the removal of surface oxides. Stainless steels are covered with a layer of chromium oxide which makes them corrosion resistant. This oxide layer results in the surface being passivated and resists further chemical treatment. The activating solution reacts with chromium oxide and enables the surfaces of the stainless steel needles to be chemically receptive to the various blackening solutions utilized in the second blackening step. Any surface contaminants present on the needles surfaces such as machine oil and grease will also be removed during this step. Various acids such as hydrochloric acid, phosphoric acid and sulfuric acid are commonly used at elevated temperature for this purpose. Therefore, the first step is also referred to as a pickling process step which typically lasts about 10 minutes to about one hour. The formulation for a pretreatment bath listed below in Table 1 was developed for a 30 second activation process adapted to an in-line process and 3 minutes for a large-scale batch process. The process temperature for this bath formulation is 80° C., well below the boiling point of the solution to prevent fume formation of hazardous material.

In the pretreatment process, a pretreatment bath solution as described above is prepared using conventional mixing equipment and process equipment. The solution is transferred to a conventional bath vessel having the desired dimensions and volumetric capacity. The pretreatment process step can be conducted as a batch process or a continuous process. It will be appreciated that the bath configuration will also depend on whether the pretreatment process is batch or continuous. In a batch process, the needles are typically loaded into a basket and immersed in the bath in the bath solution. The needles are maintained in the bath for a sufficient period of time at a sufficient temperature to effectively pretreat the surfaces of the needles. The time will typically range from about 30 seconds to about 1 hour, more typically about 1 minute to about 30 minutes, and preferably about 2 minutes to about 5 minutes, depending upon on the amount of needles in the batch. The temperature of the pretreatment bath will typically range from about 60° C. to about 100° C., more typically about 70° C. to about 90° C., and preferably about 75° C. to about 85° C.

In a continuous process, needles are typically mounted to a strip for rapid movement between manufacturing stations in a high-speed needle operation. In such a process, the strip mounted needles are moved through the pretreatment bath while mounted to the strip. The needles are maintained in the bath for a sufficient period of time at a sufficient temperature to effectively pretreat the surfaces of the needles. The time will typically range from about 20 seconds to about 60 seconds, more typically about 25 seconds to about 45 seconds, and preferably about 30 seconds to about 40 seconds. The temperature of the pretreatment bath will typically range from about 60° C. to about 100° C., more typically about 70° C. to about 80° C., and preferably about 75° C. to about 85° C.

The blackening process is performed in a similar manner to the pretreatment process. In the blackening process, a blackening bath solution as described above is prepared using conventional mixing equipment and process equipment. The solution is transferred to a conventional bath vessel having the desired dimensions and volumetric capacity. The blackening process step can be conducted as a batch process or a continuous process. It will be appreciated that the bath configuration will also depend on whether the blackening process is batch or continuous. In either case, the bath may be optionally agitated by conventional equipment. In a batch process, the needles are typically loaded into a basket and immersed in the bath in the bath solution. The quantity of needles in a batch will vary with the size of the system and may range for example from less than 10 to more than 10,000 needles. The needles are maintained in the bath for a sufficient period of time at a sufficient temperature to effectively treat the surfaces of the needles to obtain blackened surfaces. The time will typically range from about 1 minute to about 60 minutes, more typically about 2 minutes to about 30 minutes, and preferably about 2 minutes to about 4 minutes. The temperature of the blackening treatment bath will typically range from about 90° C. to about 140° C., more typically about 95° C. to about 110° C., and preferably about 98° C. to about 105° C. In a continuous process, needles are typically mounted to a strip for rapid movement between manufacturing stations in a high-speed needle operation. In such a process, the strip mounted needles are moved through the blackening bath while mounted to the strip. The needles are maintained in the bath for a sufficient period of time at a sufficient temperature to effectively blacken the surfaces of the needles. The typical number of needles in the treatment bath may range, for example, from 20 or less to 100 or more needles at one time. The treatment time will typically range from about 5 seconds to about 40 seconds more typically about 10 seconds to about 30 seconds, and preferably about 15 seconds to about 25 seconds. The temperature of the blackening treatment bath will typically range from about 90° C. to about 140° C., more typically about 95° C. to about 110° C., and preferably about 98° C. to about 105° C.

Non-Hazardous Cleaning Solution and Process

A method for oxide residue cleaning process has been developed to ensure complete or substantially complete removal of oxide residues from the surface of blackened needles. A unique feature of the new method is its short process time (as little as 30 second) for each of its steps. This makes it ideal for fully automatic batch process and a robotic equipment for large scale needle blackening process, in which a batch of 15,000 needles turns black in 2 minutes. The novel method and compositions of this invention address removal of large amounts of black oxide byproduct that are formed and deposited onto inside surfaces of coating tanks and on the blackened needles during production.

Moreover, the loose oxide layer on the surface of the blackened needles affect the adhesion between silicone lubrication layer and the needle. The silicone coating on the new black needles tend to be removed easier than the conventional needles with the same geometry, leading to poor penetration performance.

In order, to overcome this problem, the entire batch of blackened needles were placed into an ultrasonic batch containing 1% citric acid at the end of blackening process. The needles were treated at ultrasonic condition for 1 minute, prior to rinse two times in water. The short cleaning time is critical for automation process.

With regard to suitable ultrasonic baths, any commercially available ultrasonic bath systems are suitable provided that the systems are able to cause cavitation (to form microbubbles) and implosion of the formed microbubbles in the citric acid solution. The size of the bath may vary according to the number of needles to be processed. For example, a one-half gallon sized ultrasound bath is sufficiently large to treat 300 cardio needles. Commercially available ultrasonic cleaners provided by Branson Ultrasonics of Danbury, Conn., are available in one-half, three-quarter, one and one-half, two and one-half and five and one-half gallon sizes and operate at a frequency of about 40 kHz with power ratings of about 80, 130, 130, 185 and 320 watts, respectively for the aforementioned sized units.

EXAMPLE 1

6000 6 mil taper point cardio needles (BV050606D01) were blackened according to the procedure described in Example 5 of US Patent Publication 2017/0370004, the entire disclosure of which is incorporated herein by reference. The blackened needles were divided into several sets with approximately 300 needles each. Each set of needles were placed in a 1% aqueous solution of the various formulations described in Table 1 in a one-half gallon ultrasonic bath Branson ultrasonic cleaner (Model: 1510R-MTH) for 1 minute at ambient temperature. The ultrasonically cleaned needles were further rinsed in water twice before coated with 4.5% Nusil MED4162 heptane solution. The silicone coated needles were cured at 200 C for 4 hours and the silicone coating process were repeated 3 times. Each set of needles received 4 layers of silicone coatings.

Needle Test Procedure.

Coating performance for medical devices can be tested with a variety of friction or adhesion tests. In the case of surgical needles, coating performance and integrity is evaluated using a penetration testing device. A coated surgical needle is held using self-locking tweezers or a similar holding device. The coated needle is then passed through a medium that is representative of general human tissue. Approximately half of the needle length is passed through the medium and then retracted prior to the next pass. The test media is typically a type of synthetic rubber (Duraflex™, Manufacture by Monmouth Rubber and Plastic Corporation, Monmouth, N.J.). A typical test includes using 10 needles that are individually passed through the media 10 times each. The maximum force is recorded for each pass and used as a measure of the coating performance. Typically, the penetration force increases with each successive pass as the coating wears off from the needle. Further detail of the equipment and method can also be found in U.S. Pat. No. 5,181,416, the disclosure of which is incorporated herein by reference.

All 5 sets of coated needles were tested using this procedure, together with two sets of control samples. The results are summarized in TABLE 1.

TABLE 1

Penetration Test of Blackened Needles Cleaned by Various Acids in an Ultrasonic Batch for 1 Minute.

| Entry | Acid Type (1 wt. % Aqueous) | 1$^{st}$ Pass Penetration Force (g) | 10th Pass Penetration Force (g) |
|---|---|---|---|
| 1a | Citric acid | 20 | 34 |
| 1b | Acetic acid | 38 | 54 |
| 1c | Hydrochloric acid | 36 | 52 |
| 1d | Nitric acid | 36 | 51 |
| 1e | Sulphuric acid | 37 | 53 |
| Control 1 | Non-Treated | 40 | 53 |
| Control 2 | Water Rinse | 39 | 52 |

By referring to TABLE 1, citric acid is shown to provide the most effective cleaning on the blackened needles, as illustrated by the lowest needle penetration forces. Best adhesion was observed between the silicone coating and the surface of blackened needles on the citric acid cleaned needles as evidenced by the lower penetration forces. If lubricant adhesion is poor, the silicone lubrication layer on the needle will be minimum and easily removed during penetration testing as illustrated by higher penetration forces due to lack of lubricant on the needle.

EXAMPLE 2

Different concentrations of citric acid were used for the cleaning process and 8 batches of needles were cleaned with different concentrations of citric acid in an ultrasonic bath for one minute. Two more sets of control samples were also included for this experiment. The first set of control samples were immersed into 1% citric acid solution (not in ultrasonic bath, control 3). The other set of samples were cleaned in Triton™ X-100 surfactant. (Triton™ X-100 surfactant is a commercially available surfactant of Dow Chemical and comprises 0.06% of octyl phenol ethoxylate in an aqueous solution) Similar experiments were performed using the procedure described above to evaluate its efficacy toward penetration performance and the results are summarized in Table 2.

TABLE 2

Penetration Test Blackened Needles Cleaned with Various Citric Acid Concentrations

| Entry | Concentration (wt. %) | 1$^{st}$ Pass Penetration Force (g) | 10th Pass Penetration Force (g) |
|---|---|---|---|
| 2a | 0.5 | 28 | 47 |
| 2b | 0.75 | 24 | 39 |
| 1a | 1 | 20 | 34 |
| 2c | 2 | 20 | 35 |
| 2d | 3 | 19 | 34 |
| 2e | 5 | 20 | 33 |
| 2f | 10 | 17 | 33 |
| Control 3 | 1 | 35 | 51 |
| Control 4 | Triton ™ X-100 Surfactant | 41 | 56 |

Referring to Table 2, it is observed that at a citric acid concentration of 0.75% and above, sufficient removal of oxide residue on the surface of blackened needle as illustrated by the penetration test results outlined in Table 2. It was observed that the color of the cleaned needles starts to fade a when the concentration of the cleaning solution reaches 5%. Those blackened needles cleaned by 10% citric acid under ultrasonic condition for 1 minute turned into light brown color. Ultrasonic bath is needed to provide effective cleaning that the current surfactant based cleaning process does not provide for this type of blackened needles.

Different ultrasonic treatment time was explored on 1% citric acid solution to evaluate its efficacy toward penetration performance and the results are summarized in Table 3. The control experiment for non-ultrasonic condition was also included in this table.

TABLE 3

Penetration Test for Blackened Needles Cleaned with 1% Citric Acid Solution Under Different Ultrasonic Treatment Times

| Entry | Time (minute) | 1$^{st}$ Pass Penetration Force (g) | 10th Pass Penetration Force (g) |
|---|---|---|---|
| 3a | 0.25 | 29 | 38 |
| 3b | 0.5 | 23 | 35 |
| 1a | 1 | 20 | 34 |
| 3c | 3 | 18 | 33 |
| 3d | 5 | 19 | 34 |
| 3e | 10 | 17 | 30 |

Referring to Table 3, it is observed that at ultrasound treatment times of 0.5 minutes and above, sufficient removal of oxide residue from the surface of blackened needles as evidenced by the lower penetration forces results outlined in Table 3. It was also observed that the color of the cleaned needles begins to fade away when the cleaning time in the ultrasonic bath reaches 10 minutes.

In summary, a low cost, non-hazardous cleaning method was developed to remove the oxide residues on the surface of blackened needles. A combination of citric acid and/or ultrasonic agitation provides a controlled removal of loose oxide particles to provide a good balance of color and penetration performance required for surgical needles. The concentration of citric acid in the cleaning solution is safe to the worker and environment, similar to the one in soda soft drink.

Although this invention has been shown and described with respect to detailed embodiments thereof, it will be understood by those skilled in the art that various changes in form and detail thereof may be made without departing from the spirit and scope of the claimed invention.

We claim:

1. A blackened surgical needle made by the method of treating blackened surgical needles, comprising the steps of:
    a. determining that a blackening process may have produced loose black oxide particles on the blackened surgical needle;
    b. placing at least one blackened surgical needle having loose black oxide particles on its surface into a bath, wherein the bath comprises:
        i. an effective amount of citric acid to remove loose black oxide particles from the at least one blackened surgical needle; and
        ii. a source of ultrasound; and
    c. applying the ultrasound in the bath for a time sufficient to remove loose black oxide particles from the surface of the at least one needle and wherein the contents of the bath are maintained at a pH below 3.25.

2. The blackened surgical needle of claim 1, wherein the concentration of the citric acid is from about 0.5 wt. % to 5 wt. % (aqueous).

3. The blackened surgical needle of claim 2, wherein the concentration of citric acid is from about 0.75 wt. % to 5 wt. % (aqueous).

4. The blackened surgical needle of claim 3, wherein the concentration of citric acid is about 1.0 wt. % (aqueous).

5. The blackened surgical needle of any of the claims 1-4, wherein the frequency of the ultrasound is about 40 kHz.

6. The blackened surgical needle of claim 5, wherein the power of the ultrasound ranges from about 80 watts to about 320 watts.

7. The blackened surgical needle of claim 5, wherein the time for ultrasonic treatment is less than 5 minutes.

8. The blackened surgical needle of claim 6, wherein the time for ultrasonic treatment is less than 3 minutes.

9. The blackened surgical needle of claim 7, wherein the time for ultrasonic treatment is less than 1 minute.

10. The blackened surgical needle of claim 1, wherein the pH is in the range of 2.4 to 1.7.

11. The blackened surgical needle of claim 10, wherein the pH is in the range of 2.3 to 1.9.

* * * * *